(12) United States Patent
Frigg et al.

(10) Patent No.: US 6,187,007 B1
(45) Date of Patent: Feb. 13, 2001

(54) DEVICE FOR ATTACHING FRACTURED HIP-JOINT HEADS

(75) Inventors: Robert Frigg, Bettlach; Ronald Schwyn, Davos-Glaris, both of (CH)

(73) Assignee: Synthes (USA), Paoli, PA (US)

( * ) Notice: Under 35 U.S.C. 154(b), the term of this patent shall be extended for 0 days.

(21) Appl. No.: 09/230,516

(22) PCT Filed: Jul. 31, 1996

(86) PCT No.: PCT/CH96/00270

§ 371 Date: Jan. 27, 1996

§ 102(e) Date: Jan. 27, 1996

(87) PCT Pub. No.: WO98/05263

PCT Pub. Date: Feb. 12, 1998

(51) Int. Cl.⁷ .................................................. A61B 17/56
(52) U.S. Cl. ................................................. 606/72; 606/67
(58) Field of Search .................................. 606/60, 62, 64, 606/65, 66, 67, 72, 73; 623/23.11

(56) References Cited

U.S. PATENT DOCUMENTS

| | | | |
|---|---|---|---|
| 2,121,193 | 6/1938 | Hanicke | 128/92 |
| 2,627,855 * | 2/1953 | Price | 606/73 |
| 3,996,931 | 12/1976 | Callender, Jr. | 128/92 BA |
| 4,103,683 | 8/1978 | Neufeld | 128/92 BA |
| 4,441,492 * | 4/1984 | Rydell et al. | 606/72 |
| 4,494,535 * | 1/1985 | Haig | 606/72 |
| 5,116,336 | 5/1992 | Frigg | 606/65 |
| 5,269,686 | 12/1993 | James | 433/174 |
| 5,300,074 | 4/1994 | Frigg | 128/67 |
| 5,324,292 | 6/1994 | Meyers | 606/73 |
| 5,908,422 * | 6/1999 | Bresina | 606/67 |

FOREIGN PATENT DOCUMENTS

| | | |
|---|---|---|
| 587317 | 10/1933 | (DE) . |
| 757951C | 11/1953 | (DE) . |
| 41 06876 A1 | 9/1991 | (DE) . |
| 0257118 A1 | 8/1986 | (EP) . |
| 0411273 A1 | 6/1991 | (EP) . |
| 491 138 A1 | 6/1992 | (EP) . |
| WO 91/09572 | 11/1991 | (WO) . |

* cited by examiner

Primary Examiner—Pedro Philogene
(74) Attorney, Agent, or Firm—Pennie & Edmonds LLP

(57) ABSTRACT

This invention concerns a device for attaching fractured hip-joint heads. The device has an angular plate which includes a bone plate attachable to the femur and a sleeve extending at an angle from the bone plate. The device also includes an anchor bolt having a shaft insertable into the sleeve and a threaded part extending from the shaft and having a multi-pitch thread.

12 Claims, 3 Drawing Sheets

DEVICE FOR ATTACHING FRACTURED HIP-JOINT HEADS

FIELD OF THE INVENTION

The present invention relates generally to a device for internal fixation of a bone fracture, and in particular to a device for fixation of a fractured femoral head.

BACKGROUND OF THE INVENTION

Such devices are generally known as "hip screws". One such device is disclosed in German Patent Application No. A 41 06 876. The anchor screw disclosed in this application has only a single thread. U.S. Pat. No. 5,269,686 discloses a dental implant with a four-thread screw. However, the use of this dental implant for internal fixation of long bones is not taught or suggested. Finally, a femoral nail with a rotationally stable femoral neck screw is known from European Patent Application A 0 257 118. However, the nail only has a single thread.

All known prior art designs of hip screws suffer from the same disadvantage. Specifically, implantation causes substantial bone loss. As a result, any required revision surgery or subsequent second intervention is very difficult due to loss of bone. Thus, there exists a need for an improved hip screw.

SUMMARY OF THE INVENTION

The device according to the present invention has a body portion with a bone plate for attachment to the femur and a sleeve connected at an angle to the bone plate. The bone plate has screw holes for securing the bone plate to the femur. The device also includes an anchor screw having a shaft configured and dimensioned for sliding axial movement within the bore of the sleeve and a threaded coaxial section attached at an end of the shaft for securing the anchor screw in bone. The shaft may have a channel for receiving a guide wire to facilitate proper implantation of the anchor screw. The threaded section of the anchor screw has multiple threads, preferably at least four threads, and the shaft of the anchor screw has surface features which engage corresponding surface features of the sleeve to prevent rotation between the body portion and the anchor screw while allowing axial movement between the two.

The surface features of the shaft of the anchor screw may be ridges running longitudinally on the shaft and the surface features of the sleeve may be corresponding grooves in the bore of the sleeve.

In preferred embodiments, the outside diameter of the thread is between 10 mm and 14 mm. The threads may have a pitch of at least 50 mm and the cross-sectional area of the threaded section is between 10 mm$^2$ and 55 mm$^2$. The threaded section may be configured as a core with wings forming a spiral around the core. The wings preferably have a thickness between 0.5 mm and 2.0 mm.

BRIEF DESCRIPTION OF THE DRAWINGS

The advantages achieved by the invention are essentially to be seen in the fact that, thanks to the femur head device according to the invention—in spite of maintaining its axial travel in the direction of the neck—is attachable in a rotationally stable manner. Should the sliding feature of the anchor bolt in the socket be hampered, the multiple threaded section of the anchor screw, thanks to its projected cross section, prohibits a penetration of the femur head. Although the same projection surfaces could also be achieved even with a low screw pitch, the rotational stability of the femur head is not guaranteed in this case. The anchor bolt is introduced into the bones through axial force. Depending on the bone quality, this could occur by hand or with an sinking instrument. The additional advantage compared to a typical hip screw is that, thanks to the steep spiral angle of the wings, no torque is transferred onto the femur head during insertion, which prevents the dislocation of the femur head.

The invention and additional configurations of the invention are explained in even more detail with references to the partially schematic illustration of an embodiment.

Figure 1:
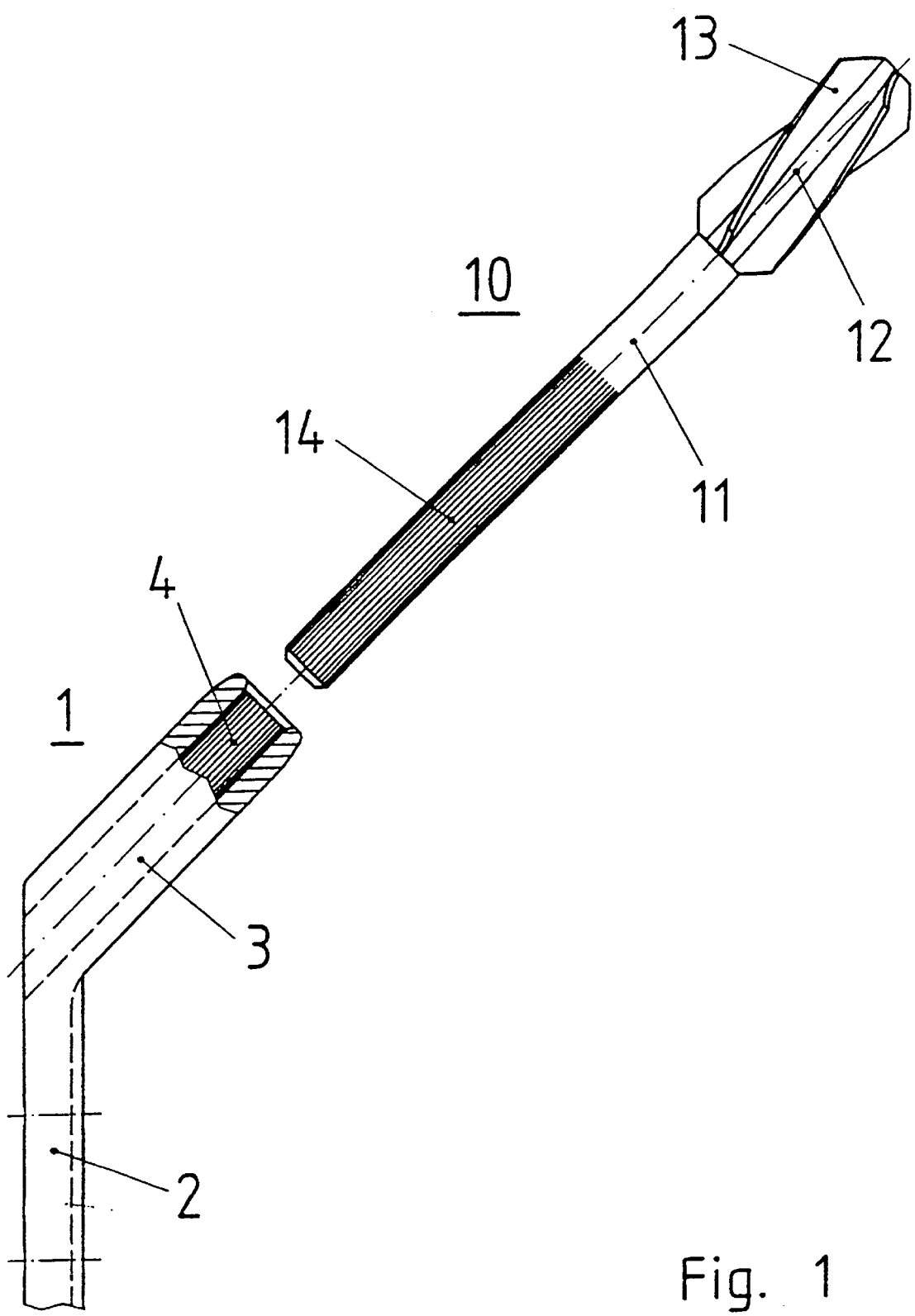

Shown are:

FIG. 1 is a perspective illustration of the unimplanted device according to the invention.

Figure 2:
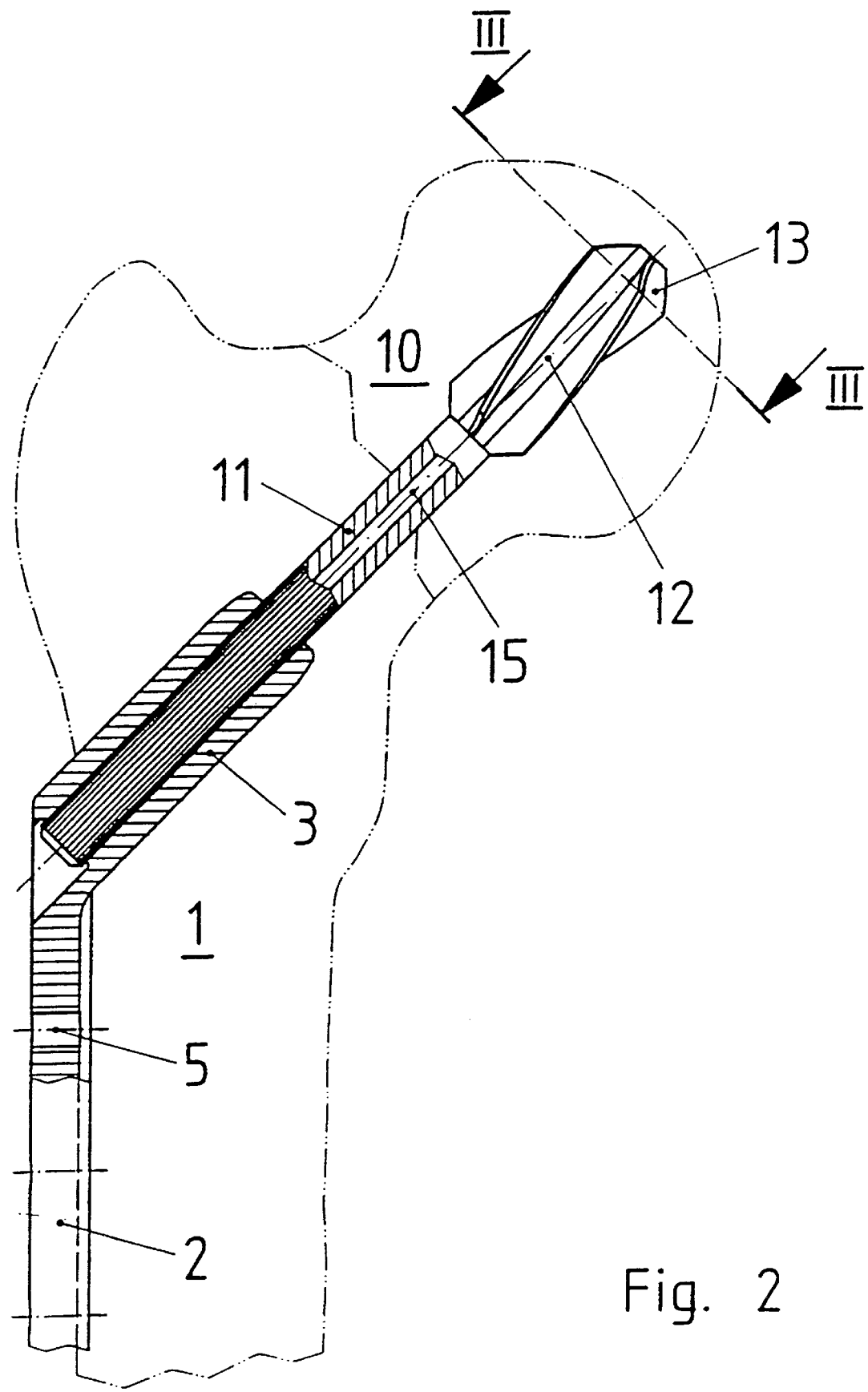

FIG. 2 is a partial cross-section through the device according to the invention implanted in the femur.

Figure 3:
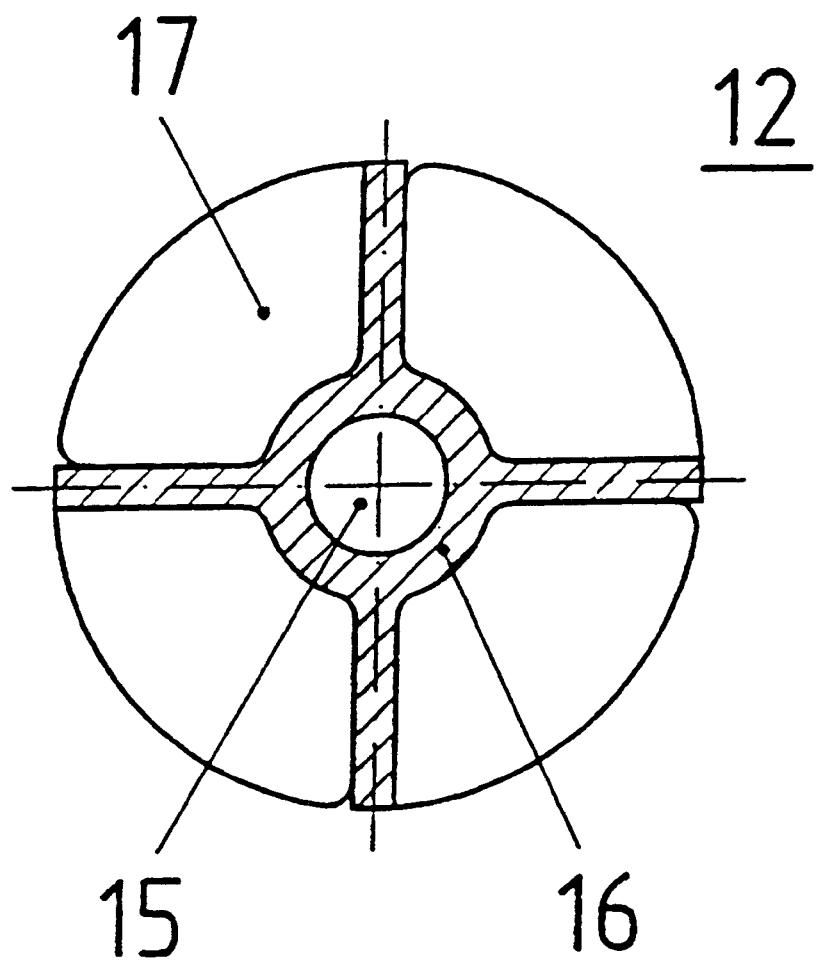

FIG. 3 is a cross-section along line III—III in FIG. 2.

DETAILED DESCRIPTION OF THE PREFERRED EMBODIMENTS

The device according to the invention represented in FIG. 1 includes essentially an angular plate 1, which comprises a bone plate 2 that can be attached to the femur and a sleeve 3 connecting at an angle to the bone plate. The device also includes an anchor bolt 10, which has a shaft 11 that can be introduced into the sleeve 3 and a coaxial threaded section 12 connecting to it.

The interior of the sleeve 3 and the outside of the shaft 11 are provided with centers 14,4—in the preferred embodiment, in the form of several longitudinal ridges 14 running axially on the shaft 11, and with it, grooves 4 correspondingly running axially in the sleeve 3—which are used for reciprocal rotational securing, while allowing axial displacement.

The threaded section 12 has a multiple, preferably four pitch thread 13. The pitch of the threading 13 amounts to at least 50 mm, preferably at least 80 mm. The outer diameter of the threading 13 amounts to 10–14 mm, preferably 11–13 mm.

As illustrated in FIG. 2, the bone plate 2 can be attached to the bone by means of uni-cortical, self-tapping screws inserted in the screw holes 5 (not shown), while the sleeve 3 comes to lie lateral to the neck fracture. In this way, the femur head can be attached to the rest of the neck in a rotationally stable manner using the anchor bolt 10. A longitudinal channel 15 that can accept a guide wire is arranged in the center of the anchor bolt 10.

As illustrated in FIG. 3, the threaded section 12 consists of a core 16 with the longitudinal channel 15 and wings 17 running in a spiral form around the core 16 The spiral angles of the individual wings are sized so that they result in the axial projection in an approximately circular cross-sectional area. The cross-sectional area of the threaded section 12 is no more than 55 mm$^2$, preferably no more than 35 mm$^2$, and at least 10 mm$^2$, preferably at least 20 mm$^2$.

The wings 17 have a thickness of at most 2.0 mm, preferably of at most 1.2 mm, and of at least 0.5 mm, preferably of at least 0.8 mm.

What is claimed is:

1. A device for internal fixation of a femoral head of a femur comprising:
    a) a body portion (1) having
        i) a bone plate (2) configured and dimensioned for attachment to the femur with at least one hole (5) for securing the bone plate (2) to the femur with a fastener and ii) a sleeve (3) connected at an angle to the bone plate (2) and having a bore (4); and b) an anchor screw (10) having
  i) a shaft (11) configured and dimensioned for sliding axial movement within the bore (4) of the sleeve (3) and
  ii) a threaded coaxial section (12) attached at an end of the shaft (11) for securing the anchor screw (10) in bone, wherein the threaded section (12) of the anchor screw (10) has multiple threads (13) and the shaft (11) of the anchor screw (10) has surface features (14) which engage corresponding surface features (4) of the sleeve (3) to prevent rotation between the body portion (1) and the anchor screw (10) while allowing axial movement between the two.

2. The device of claim 1 wherein the threaded section (12) has at least four threads (13).

3. The device according to claim 1 wherein the threads (13) have a pitch of at least 50 mm.

4. The device according to claim 1 wherein the cross-sectional area of the threaded section (12) is not greater than 55 mm².

5. The device according to claim 1 wherein the cross-sectional area of the threaded part (12) is at least 10 mm².

6. The device according to claim 1 wherein the threaded section (12) comprises a core (16) with wings (17) forming a spiral around the core (16).

7. The device according to claim 6 wherein the wings (17) brave a maximum thickness of 2.0 mm.

8. The device according to claim, 6 wherein the wings (17) have a minimum thickness of 0.5 mm.

9. The device according to claim 1 wherein the outside diameter of the thread (13) is 10 to 14 mm.

10. The device according to claim 1 wherein the outside diameter of the thread (13) is 11 to 13 mm.

11. The device according to claim 1 wherein the surface features of the shaft (11) of the anchor screw (10) comprise at least one ridge (14) running longitudinally on the shaft (11) and the surface features (4) of the sleeve (3) comprise at least one corresponding groove (4) in the bore (4) of the sleeve (3).

12. The device according to claim 1 wherein the shaft (11) of the anchor screw (10) has a channel (15) for receiving a guide wire.

* * * * *

UNITED STATES PATENT AND TRADEMARK OFFICE
CERTIFICATE OF CORRECTION

PATENT NO. : 6,187,007

DATED : February 13, 2001

INVENTORS : Robert Frigg et al.

It is certified that error appears in the above-identified patent and that said Letters Patent is hereby corrected as shown below:

On the title page at (86): change the § 371 Date from "Jan 27, 1996" to --Jan 27, 1999--.

On the title page at (86): change the § 102(3) Date from "Jan 27, 1996" to --Jan. 27, 1999--.

Column 3, line 11: after "multiple" insert --helical--.

Column 4, line 7: change "brave" to --have--.

Signed and Sealed this

Twenty-ninth Day of May, 2001

*Attest:*

NICHOLAS P. GODICI

*Attesting Officer*     *Acting Director of the United States Patent and Trademark Office*